(12) United States Patent
Vellanki et al.

(10) Patent No.: US 9,216,990 B2
(45) Date of Patent: Dec. 22, 2015

(54) CRYSTALLINE DARUNAVIR

(71) Applicant: Mylan Laboratories LTD, Hyderabad (IN)

(72) Inventors: Siva Rama Prasad Vellanki, Hyderabad (IN); Arabinda Sahu, Hyderabad (IN); Naveen Kumar Phadhuri, Hyderabad (IN); Ravindrababu Kilaru, Hyderabad (IN)

(73) Assignee: Mylan Labs Limited, Hyderbad (IN)

( * ) Notice: Subject to any disclaimer, the term of this patent is extended or adjusted under 35 U.S.C. 154(b) by 0 days.

(21) Appl. No.: 14/363,149

(22) PCT Filed: Dec. 5, 2012

(86) PCT No.: PCT/IN2012/000795
§ 371 (c)(1),
(2) Date: Jun. 5, 2014

(87) PCT Pub. No.: WO2013/114382
PCT Pub. Date: Aug. 8, 2013

(65) Prior Publication Data
US 2014/0350270 A1      Nov. 27, 2014

(30) Foreign Application Priority Data

Dec. 5, 2011   (IN) .......................... 4206/CHE/2011

(51) Int. Cl.
*C07D 493/04*      (2006.01)
(52) U.S. Cl.
CPC ................... *C07D 493/04* (2013.01)

(58) Field of Classification Search
CPC .................................................. C07D 493/04
See application file for complete search history.

(56) References Cited

U.S. PATENT DOCUMENTS 7,700,645 B2      4/2010   Vermeersch

FOREIGN PATENT DOCUMENTS

| CN | 102584844 A | 7/2012 |
| WO | WO2010086844 | 8/2010 |
| WO | WO2011048604 | 4/2011 |
| WO | WO 2011048604 A2 * | 4/2011 |
| WO | WO2011083287 | 7/2011 |
| WO | WO 2011083287 A2 * | 7/2011 |

OTHER PUBLICATIONS

Gyseghem, E. et al, "Solid state characterization of the anti-HIV drug TMC114: Interconversion of amorphous TMC114, TMC114 ethanolate and hydrate", European Journal of Pharmaceutical Sciences, 2009, 489-497, 38, Elsevier B.V.
Written Opinion of the International Searching Authority, PCT/IN2012/000770, (c) Feb. 24, 2015.

* cited by examiner

*Primary Examiner* — Andrew D Kosar
*Assistant Examiner* — John S Kenyon
(74) *Attorney, Agent, or Firm* — Beck & Thomas, P.C.

(57) ABSTRACT

The present invention relates to a non-solvated crystalline Darunavir, process for its preparation and pharmaceutical composition comprising it. The present invention also relates to a process for the preparation of amorphous Darunavir from a non-solvated crystalline Darunavir.

10 Claims, 4 Drawing Sheets

CRYSTALLINE DARUNAVIR

This is a national stage entry under 35 U.S.C. §371 of International Application PCT/IN2012/000795, with an international filing date of Dec. 5, 2012, which in turn claims priority to Indian Application No. 4206/CHE/2011, filed Dec. 5, 2011 and incorporates by reference in its entirety the PCT and Indian Application into the current nonprovisional application.

This application claims priority to Indian patent application numbered 4206/CHE/2011 filed on Dec. 5, 2011 the contents of which are incorporated by reference in their entirety.

FIELD OF THE INVENTION

The present invention relates to a non-solvated crystalline Darunavir, process for its preparation and pharmaceutical composition comprising the same. The present invention also relates to a process for the preparation of amorphous Darunavir from a non-solvated crystalline Darunavir.

BACKGROUND OF THE INVENTION

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections. Darunavir has HIV protease inhibitory activity and is particularly well suited for inhibiting HIV-I and HIV-2 viruses. Darunavir, chemically (1S,2R,3'R,3'aS,6'aR)-[3'hexahydrofuro[2,3-b]furanyl-[3-(4-aminobenzenesulfonyl)isobutylamino[1-benzyl-zhydroxypropyl]carbamate. Darunavir is represented by the following structure:

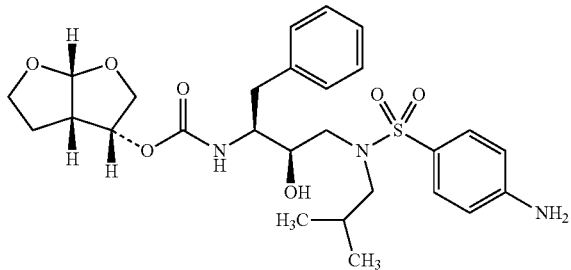 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir and its pharmaceutically acceptable salts were disclosed in U.S. Pat. No. 6,248,775, wherein Darunavir is prepared by condensing 2R-hydroxy-3-[[(4-aminophenyl)sulfonyl](2-methylpropyl)amino]-1S(phenylmethyl)propylamine with hexahydro-furo[2,3-b]furan-3-ol in anhydrous acetonitrile in the presence of anhydrous pyridine and N,N'-disuccinimidyl carbonate at ambient temperature.

U.S. Pat. No. 7,700,645 disclosed amorphous Darunavir, various solvates of Darunavir including ethanolate and method for their preparation as well as their use as a medicament. Journal of Organic Chemistry 2004, 69, 7822-7829 disclosed amorphous Darunavir is obtained by purification with column chromatography in 2% methanol in chloroform as eluent.

PCT publication WO2010086844A1 disclosed crystalline dimethylsulfoxide solvate and crystalline tetrahydrofuran solvate of darunavir. The publication also disclosed the amorphous darunavir having the IR spectrum with characteristic peaks at about 1454 and 1365 $cm^{-1}$ PCT publication WO2011083287A2 disclosed crystalline darunavir hydrate substantially free of any non aqueous solvent.

Though many solvates or hydrates are reported in the prior art, anhydrous crystalline Darunavir is not disclosed in the literature. Thus there exist a need in the art for exploration of new polymorphic forms with improved bioavailability and pharmaceutical activity. The inventors of the present invention have developed a novel crystalline form of Darunavir.

SUMMARY OF THE INVENTION

One aspect of the present invention is to provide a non-solvated crystalline Darunavir.

Another aspect of the present invention is to provide a non-solvated crystalline Darunavir which is characterized by powdered X-ray diffraction pattern.

Yet another aspect of the present invention is to provide a process for the preparation of a non-solvated crystalline Darunavir.

Yet another aspect of the present invention is to provide a dimethylformamide solvate of Darunavir.

Yet another aspect of the present invention is to provide a dimethylformamide solvate of Darunavir which is characterized by powdered X-ray diffraction pattern.

Yet another aspect of the present invention is to provide a process for the preparation dimethylformamide solvate of Darunavir.

Yet another aspect of the present invention is to provide a process for the preparation of amorphous Darunavir from non-solvated crystalline Darunavir.

DETAILED DESCRIPTION OF THE INVENTION

Figure 1:
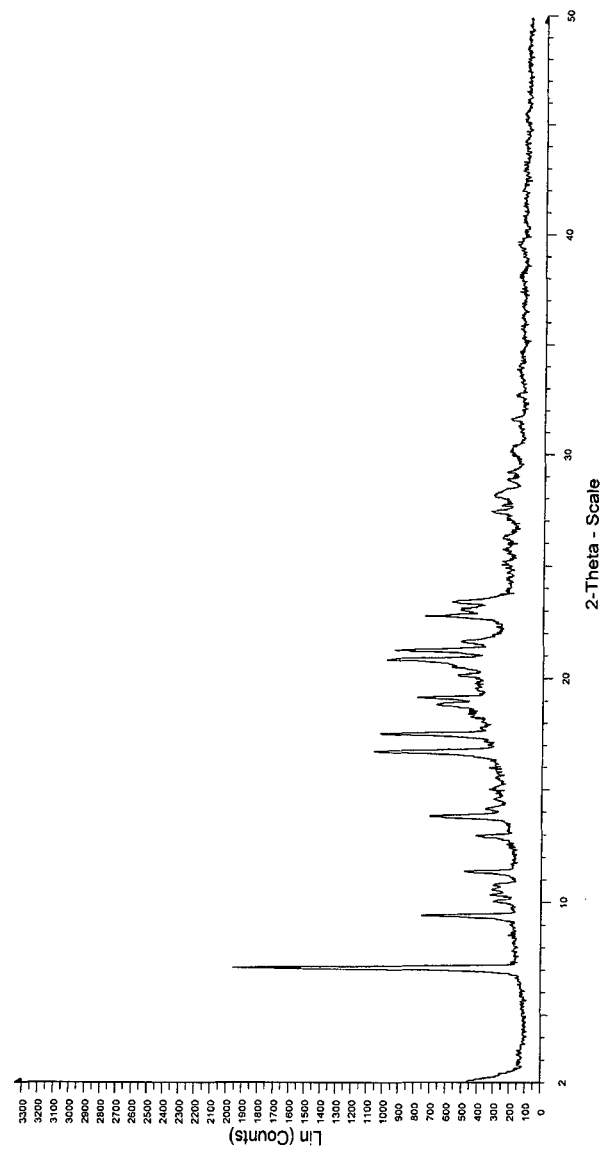
FIG. 1 is a representative X-ray diffraction pattern of non-solvated crystalline Darunavir.

The present invention relates to a non-solvated crystalline Darunavir and its process for its preparation using solvent and anti-solvent technique. The present invention is further relates to a process for the preparation of amorphous Darunavir from a non-solvated crystalline Darunavir.

One embodiment of the present invention is to provide a non-solvated crystalline Darunavir, characterized by Powder X-ray diffraction pattern having 2θ angle positions at about 7.03, 13.77, 16.67, 17.48, 19.12, 21.22, 21.61 and 22.75±0.2 degrees and the non-solvated crystalline Darunavir further characterized by Powder X-ray diffraction pattern having 2θ angle positions at about 9.36, 11.32, 12.88, 18.82, 20.12, 23.04, 23.38, and 25.11±0.2 degrees.

Yet another embodiment of the present invention is to provide non-solvated crystalline form of Darunavir, showed an endothermic peak in differential scanning calorimetry at ~75° C.

Yet another embodiment of the present invention is to provide a dimethylformamide solvate of Darunavir, characterized by Powder X-ray diffraction pattern having 2θ angle positions at about 6.84, 8.83, 16.27, 17.85, 18.58, 22.15, 22.56 and 22.96±0.2 degrees the dimethylformamide solvate of Darunavir further characterized by Powder X-ray diffraction pattern having 2θ angle positions at about 10.30, 10.96, 13.61, 13.83, 16.75, 18.58, 19.38, 19.84, 20.23, 20.74, 26.34, 27.51, 28.48 and 28.98±0.2 degrees.

Yet another embodiment of the present invention is to provide a dimethylformamide solvate of Darunavir, showed an endothermic peak in differential scanning calorimetry at ~88° C.

Yet another embodiment of the present invention is to provide a process for the preparation of non-solvated crystalline Darunavir comprising the steps of:
 a) dissolving Darunavir in an ester solvent,
 b) adding an anti solvent, and
 c) isolating non-solvated crystalline Darunavir.

According to the present invention, Darunavir is dissolved in an ester solvent is selected from ethyl acetate, methyl acetate or butylacetate and an anti solvent selected from hexane, heptane or cyclohexane is added, then maintained the reaction for about 8 to 12 hours and isolated the obtained solid to get crystalline Darunavir.

Yet another embodiment of the present invention is to provide a process for the preparation of
 a) dissolving Darunavir in dimethylformamide,
 b) adding water as an anti solvent, and
 c) isolating dimethylformamide solvate of Darunavir.

According to the present invention, Darunavir is dissolved in dimethylformamide solvent, the reaction mass is cooled to about 0 to 35° C. and water is added as an anti solvent then maintained the reaction for about 8 to 12 hours and isolated the obtained solid.

The isolation of crystalline Darunavir may be performed by conventional techniques such as filtration or centrifugation.

According to present invention, the non-solvated crystalline Darunavir is stable at 40° C./75% RH (relative humidity) and is free from any solvates or hydrates.

Yet another embodiment, the present invention is to provide a process for the preparation of amorphous Darunavir comprising the steps of:
 a. dissolving non-solvated crystalline Darunavir in a solvent,
 b. removing the solvent and
 c. isolating amorphous Darunavir.

According to the present invention, Darunavir is dissolved in a solvent selected from dichloromethane, chloroform, carbon tetrachloride, dichloroethane, tetrahydrofuran, methanol, ethanol, isopropyl alcohol, acetonitrile, ethyl acetate or mixtures thereof and then solvent is removed by conventional techniques such as distillation, evaporation, spray drying, freeze drying, lyophilisation or agitated thin film drier (ATFD) and thus isolating amorphous Darunavir.

According to the present invention, Darunavir used for the preparation of amorphous Darunavir is either non-solvated crystalline Darunavir or dimethylformamide solvate of Darunavir.

According to the present invention is to provide a pharmaceutical composition comprising a non-solvated crystalline Darunavir and a pharmaceutically acceptable excipient.

According to the present invention, process for the preparation of amorphous Darunavir is as shown in below scheme.

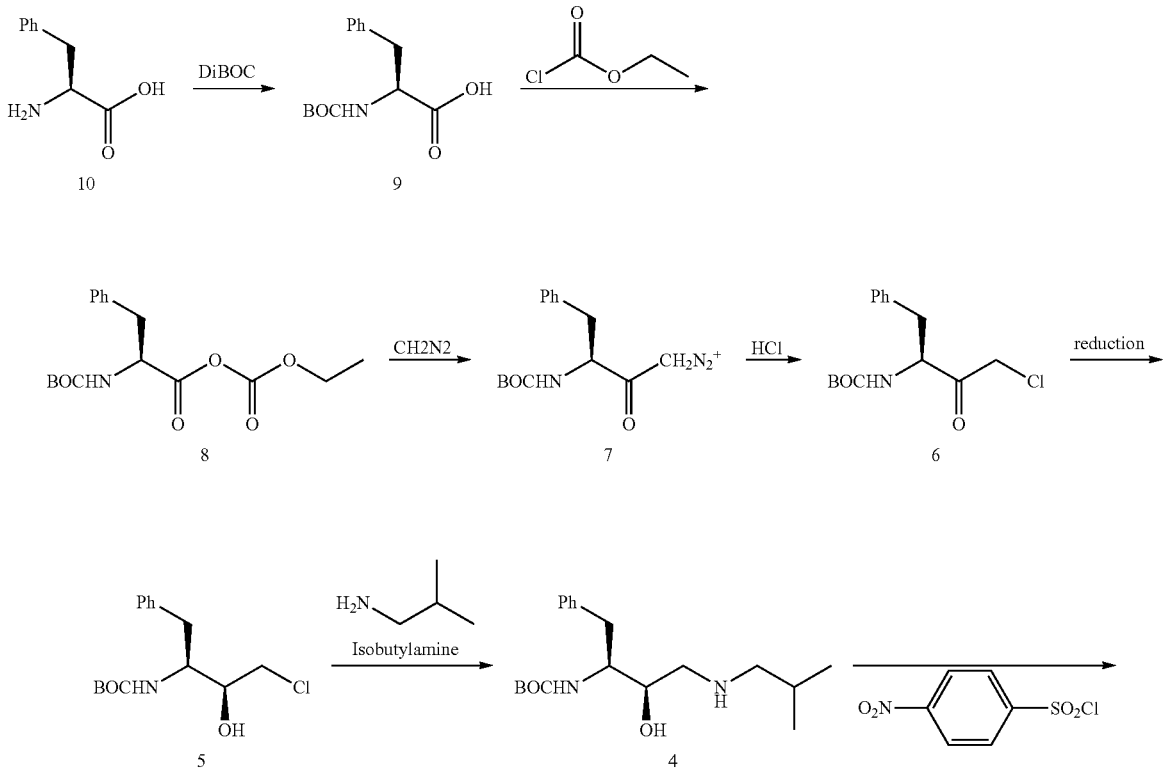

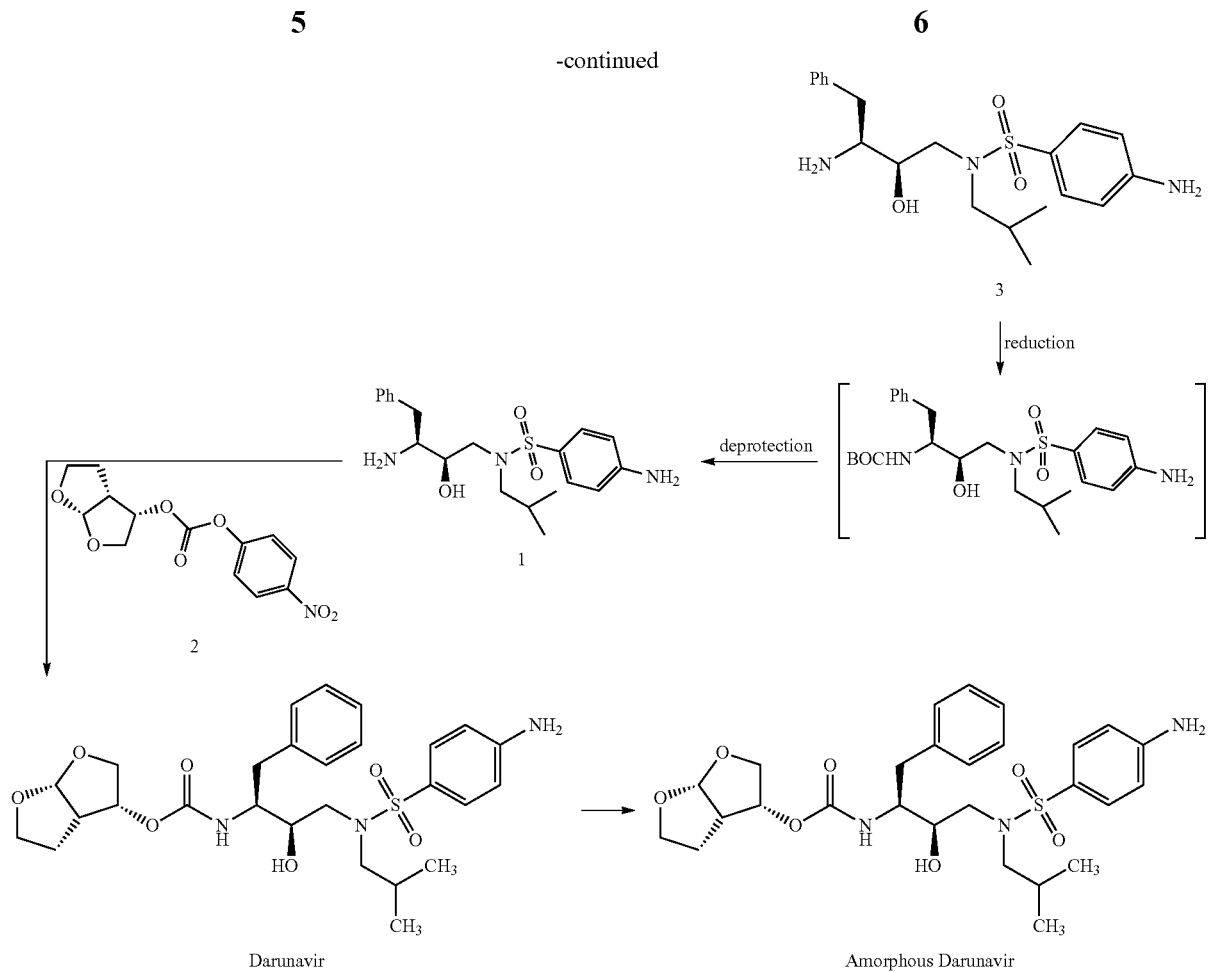
Process for the preparation of intermediate 2 is as shown in below scheme.
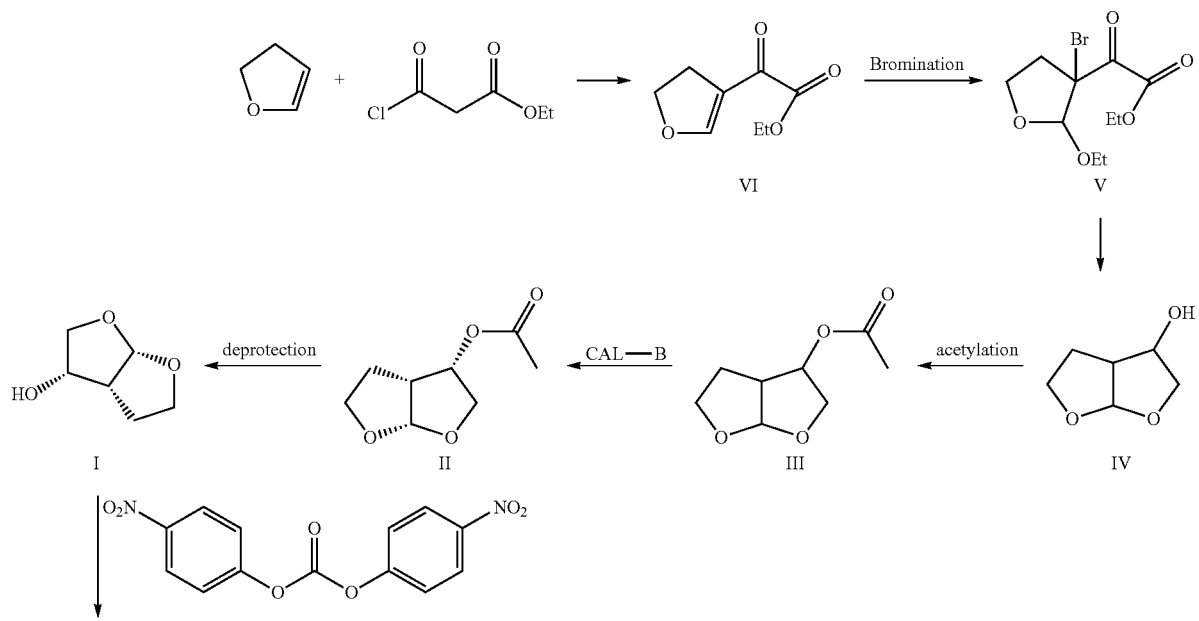

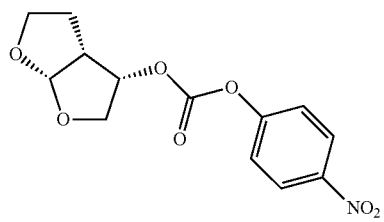

2

The following examples are provided for illustrative purposes only and are not intended to limit the scope of the invention in any way.

EXAMPLES

Example 1

Preparation of [(1S,3S)-3-chloro-2-hydroxy-1-(phenylmethyl)propyl]carbamic acid tert-butyl ester (5)

The solution of (3S)-3-(tert-butoxycarbonyl)amino-1-chloro-4-phenyl-2-butanone (Chloromethyl ketone 6, 100 g) and aluminium isopropoxide (35 g) in isopropylalcohol was heated to mild reflux and maintained for 3 hours. After completion of reaction distilled off isopropyl alcohol up to 50% under vacuum and the resultant mass was cooled to 25-35° C. Water was added to the distillate, pH was adjusted to 3.0-4.0 with acetic acid and maintained the stirring for 2 hours at 25-35° C. The obtained solid was filtered and washed with water. The wet cake was taken into isopropyl alcohol (400 mL) and heated to reflux for 60 minutes, the mass was cooled to 25-35° C. again maintain the stirring for 60 minutes, the obtained solid was filtered and washed with isopropyl alcohol. The wet product was dried under normal drying to get title compound 5 (yield 80 g).

Example 2

Preparation of [(1S,2R)-3-[(2-methylpropyl)amino]-2-hydroxy-1-(phenylmethyl)propyl]carbamic acid tert-butyl ester (4)

The mixture of [(1S,2S)-3-chloro-2-hydroxy-1-(phenylmethyl)propyl]carbamic acid tert-butyl ester (5, 100 g), isobutyl amine (294 g), sodium carbonate (31.3 g) and water was heated to 60-65° C. and maintained for 3 hours. After completion of reaction water (200 mL) was added and distilled out excess isobutyl amine under vacuum at below 75° C. Water (800 mL) was added to the distillate, cooled to 25-35° C. and stirred for 2 hours. The obtained solid was filtered and washed with water to get title compound 4 (yield 105 g).

Example 3

Preparation of [(1S,2R)-3-[[(4-nitrophenyl)sulfonyl](2-methylpropyl)amino]-2-hydroxy-1-(phenylmethyl)propyl]carbamic acid tert-butylester (3)

[(1S,2R)-3-[(2-methylpropyl)amino]-2-hydroxy-1-(phenyl methyl)propyl]carbamic acid tert-butyl ester (4, 100 gm) and triethylamine (39.04 g) was added to methylenedichloride (1200 mL) and the temperature was raised to 40° C. p-nitro benzene sulfonyl chloride solution (72.3 g of p-NBSC dissolve in 300 mL methylenedichloride) was added slowly at 40-45° C. for 2-3 hrs. The reaction was maintained for 3 hours at 40-45° C. After completion of the reaction, water (500 mL) was added, separated the organic layer and distilled out methylene dichloride at atmospheric pressure. Finally, strip out the methylene dichloride by using isopropyl alcohol (200 mL). Isopropyl alcohol (1000 mL) was added to the distillate and maintained the stirring for 60 minutes at 70-80° C. Cooled the mass to 30-35° C., filtered and washed with Isopropyl alcohol to get title compound 3 (yield 145 g).

Example 4

Preparation of 4-Amino-N-(2R,3S)(3-amino-2-hydroxy-4-phenylbutyl)-N-isobutyl-benzene sulfonamide (1)

(1S,2R)-{1-benzyl-2-hydroxy-3-[isobutyl-(4-nitro-benzenesulfonyl)-amino]-propyl}-carbamic acid tert-butyl ester (3, 100 g), 10% palladium carbon (10 gm) and triethanolamine (2 gm) were suspended in isopropyl alcohol. The reaction was heated to 40-45° C. and maintained under 4-6 kg/cm2 of hydrogen pressure for 3 hours. After completion of reaction, the mass was filtered and hydrochloric acid (70 mL) was added to the filtered mass. The solution was heated to reflux and maintained for 2-3 hours. After completion of reaction the mass was cooled to 25-35° C., the reaction mass pH was adjusted to 6.0-7.0 with 20% sodium hydroxide solution and distilled out isopropyl alcohol under vacuum at below 55° C. Ethanol (200 mL) and water (400 mL) was added to the distillate, the mass pH was adjusted to 9.0-10.0 with 20% sodium hydroxide solution at 25-35° C. and maintained the stirring for 2 hours at 25-35° C. The mass was cooled to 0-5° C., filtered and wash with water. The wet product was taken into ethanol (350 mL), maintained the stirring for 30 minutes at reflux temperature. The mass was cooled to 2-4° C., stirred for 2 hours, filtered and washed with ethanol (50 mL). The wet product was dried under normal drying to get title compound 1 (Yield 60 g).

Example 5

Preparation of ethyl-2-(4,5-dihydrofuran-3-yl)-2-oxoacetate (VI)

2,3-Dihydrofuran (250 g) was taken in toluene (2000 mL) and triethyl amine (505 g) was added to above solution. Ethyl oxalyl chloride (536.5 g) was slowly added to the above mixture by maintaining temperature at 25-30° C. and maintained the stirring for 5 hours. After completion of reaction separated the organic layer, washed the organic layer with 8% sodium bicarbonate solution (2×500 mL). Organic layer was distilled completely under vacuum to get title compound VI (Yield 560 g).

1H NMR: 1.38 (t, 3H), 2.93 (t, 2H), 4.34 (q, 2H), 4.63 (t, 2H), 8.02 (s, 1H).

Example 6

Preparation of ethyl-2-(3-bromo-2-ethoxytetrahydrofuran-3-yl)-2-oxoacetate (V)

Ethyl-2-(4,5-dihydrofuran-3-yl)-2-oxoacetate (VI, 100 g) was dissolved in dichloromethane (500 ml) and Ethanol (150 mL) was added. The reaction mass was cooled to 5 to 10° C. N-bromosuccinimide (115 g) was added lot wise by maintaining temp below 10° C. Reaction mass was then stirred at 20-30° C. till completion of reaction. Reaction mass was washed with sodium bicarbonate solution (2%, 3×400 mL) and the organic layer was used for the next step.

Example 7

Preparation of hexahydrofuro[2,3-b]furan-3-ol (IV)

To the solution of Ethyl-2-(3-bromo-2-ethoxy tetra hydrofuran-3-yl)-2-oxoacetate in dichloromethane (V, 500 mL) as prepared in above example, sodium sulphite solution (225 g was dissolved in 1700 mL of water) was added at 25-35° C. Reaction mass was stirred for 5-8 hours at the same temperature and separated the organic and aqueous layers. Organic layer was washed with water (340 mL). Distilled out the solvent completely get ethyl-2-(2-ethoxy tetra hydrofuran-3-yl)-2-oxoacetate. Sodium borohydride (35.5 g) was dissolved in ethanol (400 mL) under nitrogen atmosphere, ethyl-2-(2-ethoxytetra hydrofuran-3-yl)-2-oxoacetate was dissolved in ethanol (100 mL) and slowly added to above solution at 15-30° C. Reaction mass was heated to 30-45° C., maintained for 5-8 hours, the reaction mass temperature was raised to 55° C. and stirred for 8 hours. The reaction mass was cooled to 20-30° C., ammonium chloride solution (115 g in 200 mL water) was slowly added and stirred for 1-2 hours. The reaction mass was filtered and filtrate was distilled out under vacuum to get residue. Dichloromethane (600 mL) was added to residue and cooled to −10° C. Hydrochloric acid (85 mL) was added slowly drop wise in 2 hours by maintaining temp −5 to 0° C., reaction mass was stirred for 60 minutes at −5 to 0° C. and distilled the solvent completely. The obtained residue was stripped out with isopropyl alcohol (2×200 mL, 1×100 mL), ethyl acetate (500 mL) was added to the resultant residue, stirred for 30-60 minutes and cooled to 10-15° C. The solution was filtered and filtrate was concentrated to get title compound IV (yield 56 g).

Example 8

Preparation of Hexahydrofuro[2,3-b]furan-3-yl acetate (III)

Hexahydrofuro[2,3-b]furan-3-ol (IV, 60 g) was dissolved in dichloromethane (300 mL) and cooled to 0-5° C. To the cooled solution triethylamine (58.2 g), N,N-dimethylaminopyridine (1.12 g) was added, acetic anhydride (56.5 g) was added for 30-60 minutes at the same temperature, the mass temperature was raised to 25-35° C. and stirred for 2-4 hours. After completion of reaction the mass was cooled to 10-20° C., water (120 mL) was added, stirred for 30 minutes, separated the organic layer, washed with 10% sodium chloride solution (120 mL) and distilled out dichloromethane to get title compound (yield 72 g). Further, the product was purified by fractional distillation to get pure Hexahydrofuro[2,3-b]furan-3-yl acetate III (yield 54 g).

1H NMR: 1.9-2.09 (m, 2H), 2.10 (s, 3H), 3.0-3.1 (m, 1H), 3.86-4.03 (m, 2H), 3.73 (dd, 1H), 4.10 (dd, 1H), 5.19 (m, 1H), 5.72 (d, 1H)

Example 9

Preparation of (3R,3aS,6aR)-Hexahydrofuro[2,3-b]furan-3-yl acetate (II)

To the buffer solution (104.3 g of sodium dihydrogen orthophosphate dissolved in 530 mL of water & pH adjusted to 6.0-6.5 with saturated sodium bicarbonate solution (68 g in 680 mL water) solution) hexahydrofuro[2,3-b]furan-3-yl acetate (III, 115 g) and CAL-B (17.25 g) was added at 25-35° C., heated to 38-45° C. and stirred for 24 hours. CAL-B (17.25 g) was added stirred for 16 hours, again CAL-B (11.5 g) was added at 38-45° C. and stirred for 16 hours (pH should maintain 6.0-6.5). The reaction mass was cooled to 20-30° C., methylenedichloride (1150 mL) was added to the mass and stirred for 30 minutes. The reaction mass was filtered through hyflowbed then separated the organic layer and washed with 10% sodium chloride solution (575 mL). Organic layer was distilled completely under vacuum to get title compound II (yield 40.0 g).

Example 10

Preparation of (3R,3aS,6aR)-Hexahydrofuro[2,3-b]furan-3-ol (I)

(3R,3aS,6aR)-Hexahydrofuro[2,3-b]furan-3-yl acetate (II, 14.0 g) was dissolved in methanol (42 mL). Potassium carbonate (0.34 g) was added and stirred at 25-35° C. for 6-8 hours. Methanol was distilled out completely under vacuum, to the distillate methylenedichloride (28 mL) was added, stirred the mass for 30 minutes and again distilled the solvent to get residue. Dissolved the residue in dichloromethane (56 mL), the resultant solution was treated with carbon and the solvent was completely distilled out get title compound I (yield 10.5 g).

Example 11

Preparation of (3R,3aS,6aR)-Hexahydrofuro[2,3-b]-furan-3-yl-4-nitrophenyl carbonate (2)

To the solution of (3R,3aS,6aR)-Hexahydrofuro[2,3-b]furan-3-ol (1,100 g) and Bis-nitrophenyl carbonate (257.2 g) in methylene dichloride (1200 mL), triethylamine solution (132 g in 300 mL of methylene dichloride) was added slowly at 20-30° C. for 2-3 hours. Maintained the reaction at the same temperature for 8-10 hours, after completion of reaction water (500 mL) was added for 30-60 minutes and settled the reaction mass then separated the organic layer. Organic layer was washed with 10% acetic acid (100 mL) and 10% sodium chloride solution (500 mL), distilled the organic layer and co distilled with ethyl acetate (100mL). Ethyl acetate (300 mL) was added to the distillate and heated to 50-55° C. for 30-45 minutes to get clear solution, the solution was cooled to 5-10° C. and maintained at the same temperature for 60 minutes. The obtained solid was filtered, washed with ethanol (100 mL) and dried the wet material at 40-45° C. for 10-14 hours to get title compound 2 (yield 160 g).

Example 12

Preparation of Dimethylformamide Solvate of Darunavir

To a mixture of 4-amino-N-(2r,3S)(3-amino-2-hydroxy-4-phenylbutyl)-N-Isobutyl-benzenesulfonamide (1, 25 g) and N-methyl-2-pyrrolidinone (NMPO, 50 mL), a solution of (3R,3aS,6aR)-Hexahydrofuro[2,3-b]furan-3-yl-4-nitrophenyl carbonate (2, 18.85 g) and N-methyl-2-pyrrolidinone (75 mL) was added at −5 to 0° C. for 2 to 3 hours under nitrogen atmosphere. The mass temperature was slowly raised to 25 to 30° C. and stirred for 6 to 8 hours. The reaction mass was quenched in to the solution of methylene chloride (125 mL) and water (250 mL) at 25-35° C. for 30 to 45 minutes. Separated the organic layer followed by washed with 10% sodium carbonate solution (150 mL), 10% sodium chloride solution (150 mL) and with water (6×150 mL). Organic layer was dried over sodium sulphate and distill off the solvent under vacuum at below 50° C. to obtain darunavir as a residue. To the residue N,N-dimethyl formamide (50 mL) was added and cooled to 0 to −5° C., water (2 mL) was added to the solution and maintained for 12 hours at 0 to −5° C., the obtained solid was filtered and washed with pre-cooled mixture of N,N-dimethyl formamide & water (25 mL+25 mL) to get dimethylformamide solvate of darunavir.

Example 13

Preparation of Non-Solvated Crystalline Darunavir

To a mixture of 4-amino-N-(2r,3S)(3-amino-2-hydroxy-4-phenylbutyl)-N-Isobutyl-benzenesulfonamide (1, 25 g) and N-methyl-2-pyrrolidinone (NMPO, 50 mL), a solution of (3R,3aS,6aR)-Hexahydrofuro[2,3-b]-furan-3-yl-4-nitrophenyl carbonate (2, 18.85 g) and N-methyl-2-pyrrolidinone (75 mL) was added at −5 to 0° C. for 2 to 3 hours under nitrogen atmosphere. The mass temperature was slowly raised to 25-30° C. and stirred for 6 to 8 hours. The reaction mass was quenched in to the solution of methylene chloride (250 mL) and water (250 mL) at 25-35° C. for 30-45 minutes. Separated the organic layer followed by washed with 10% potassium carbonate solution (5×125 mL), water (5×125 mL), 20% sodium chloride solution (25 mL), finally washed with 20% citric acid solution (125 mL). The organic layer was treated with carbon and distilled off the solvent under vacuum at below 50° C. to obtain darunavir as a residue. To the residue ethylacetate (250 mL) was added and cooled to 0 to −5° C., to the cooled solution hexane (225 mL) was added and maintained for 12 hours at 0 to −5° C., the obtained solid was filtered, washed with pre-cooled mixture of ethylacetate and hexane (25 mL+25 mL) and dried the compound to get non-solvated crystalline darunavir (yield 25 g).

Example 14

Preparation of Amorphous Darunavir

Darunavir (200 g) as obtained in above example was dissolved in methylene dichloride (10 L) and washed with water (3×1000 mL). Organic layer was taken into agitated thin film dryer (ATFD) feed tank. Applied initial temperature about 36-40° C. and high vacuum (580 mm/Hg) to the vessel. Slowly feed the solution to the Vessel (feed rate 5 L/hr) over 1 hour finally given the methylene chloride (3 L) flushing. The material is collected in the material collector. Dried at 58-62° C. for 40 hours to get amorphous darunavir (yield 160 g).

We claim:

1. A non-solvated crystalline darunavir characterized by powder X-ray diffraction pattern having 2θ angle positions at about 7.03, 13.77, 16.67, 19.12, 21.22 and 22.75±0.2 degrees.

2. The non-solvated crystalline darunavir of claim 1, further characterized by a powder X-ray diffraction pattern as depicted in FIG. 1.

3. A non-solvated crystalline darunavir characterized by a DSC thermogram with endothermic peak at about 75° C.

Figure 2:
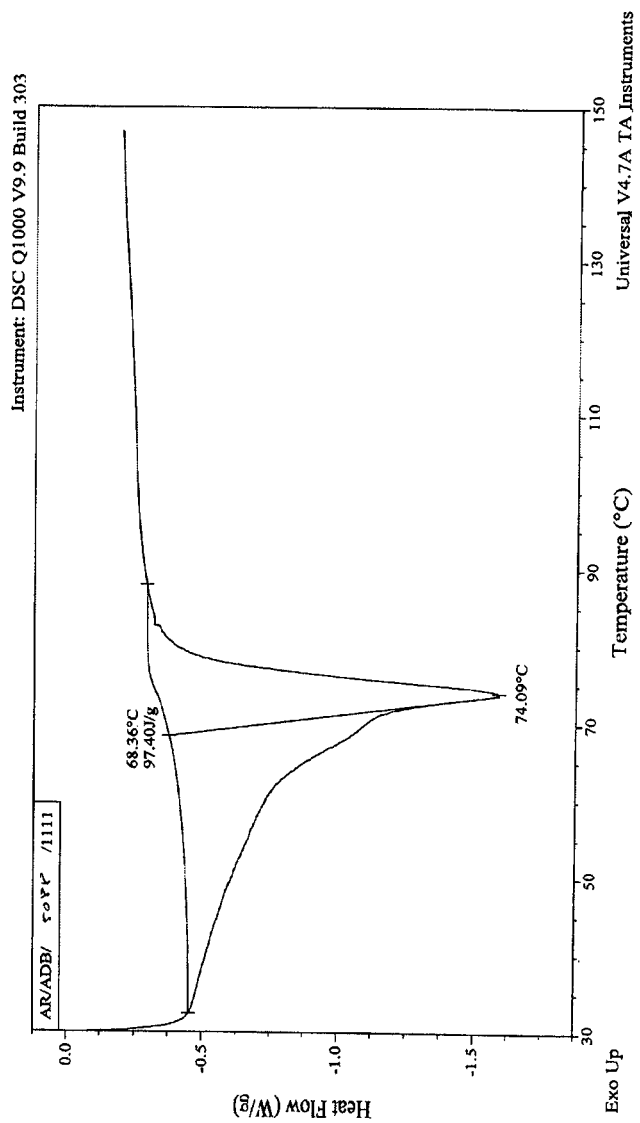
FIG. 2 is a representative DSC thermogram of non-solvated crystalline Darunavir.
Figure 3:
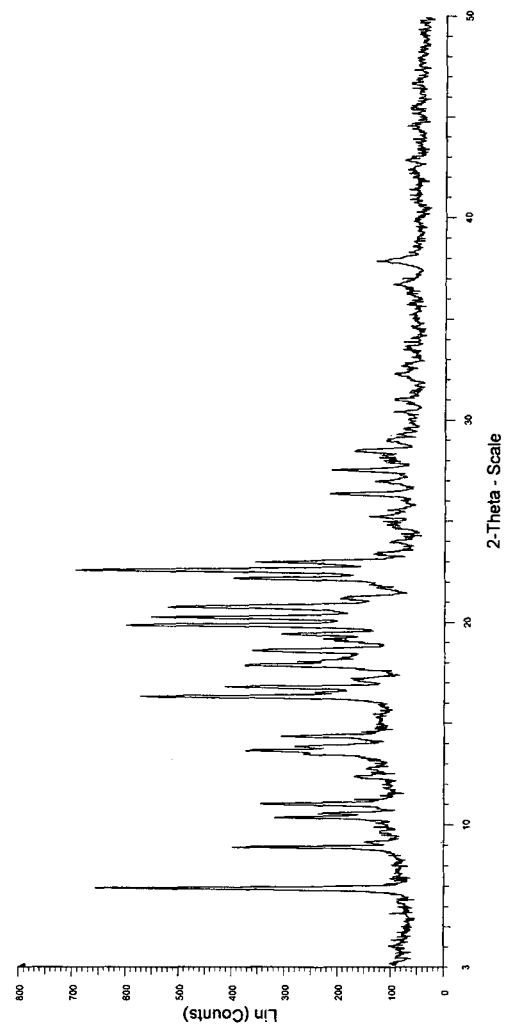
FIG. 3 is representative X-ray diffraction pattern of dimethylformamide solvate of Darunavir
Figure 4:
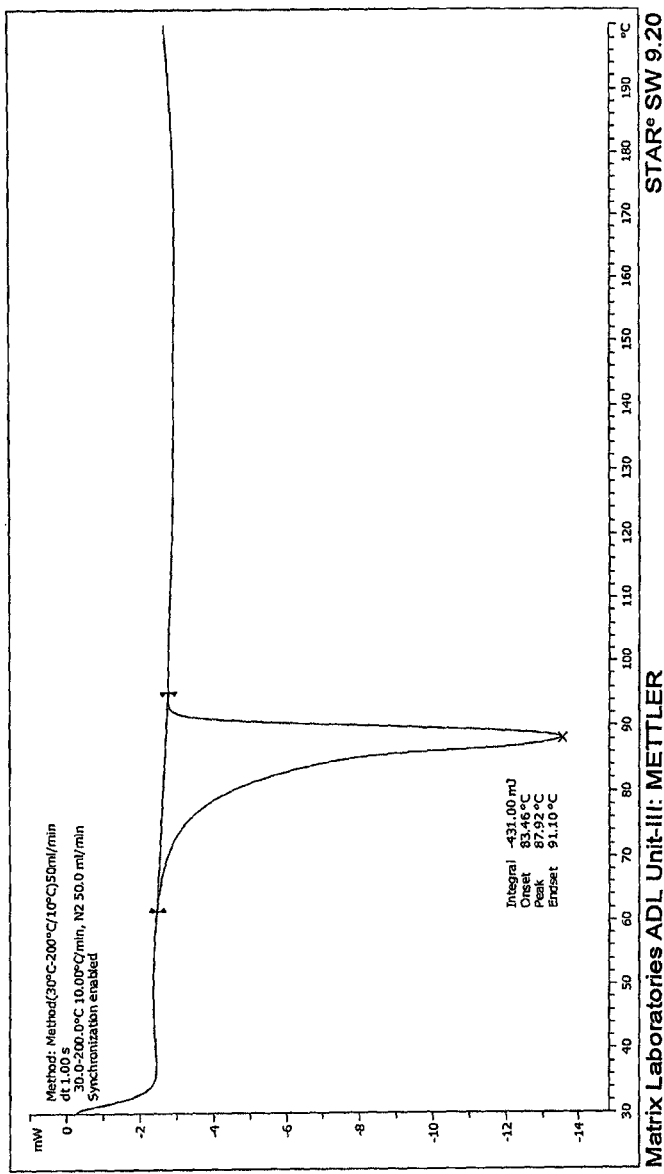
FIG. 4 is a representative DSC thermogram of dimethylformamide solvate of Darunavir.

4. The non-solvated crystalline darunavir according to claim 3, further characterized by a DSC thermogram as depicted in FIG. 2.

5. A process for the preparation of non-solvated crystalline Darunavir comprising the steps of:
  a) dissolving Darunavir in an ester solvent,
  b) adding an anti solvent, and
  c) isolating non-solvated crystalline Darunavir.

6. The process according to claim 5, wherein the solvent is selected from ethyl acetate, methyl acetate or butyl acetate and anti solvent is selected from hexane, heptane or cyclohexane.

7. A process for the preparation of amorphous Darunavir comprising the steps of:
  a) dissolving non-solvated crystalline Darunavir in a solvent,
  b) removing the solvent, and
  c) isolating amorphous Darunavir.

8. The process according to claim 7, wherein the solvent used for the dissolution of Darunavir is selected from chloromethane, chloroform, carbon tetrachloride, dichloroethane, tetrahydrofuran, methanol, ethanol, isopropyl alcohol, acetonitrile, ethyl acetate or mixtures.

9. The process according to claim 7, wherein the solvent is removed by distillation, evaporation, spray drying, freeze drying, lyophilisation or agitated thin film drier (ATFD).

10. The non-solvated crystalline darunavir according to claim 1, wherein the non-solvated crystalline darunavir is free from any solvent.

\* \* \* \* \*